United States Patent [19]

Nicholas

[11] 4,381,434
[45] * Apr. 26, 1983

[54] PRESSURE OPERATED ELECTRIC SWITCH AND ALARM SYSTEM USING SUCH SWITCH

[76] Inventor: Noel Nicholas, 6, Verona Villas, O'Connell Ave., Limerick, Ireland

[*] Notice: The portion of the term of this patent subsequent to Apr. 21, 1998, has been disclaimed.

[21] Appl. No.: 217,605

[22] Filed: Dec. 18, 1980

Related U.S. Application Data

[63] Continuation-in-part of Ser. No. 907,461, May 19, 1978, Pat. No. 4,263,586, which is a continuation-in-part of Ser. No. 826,957, Aug. 22, 1977, abandoned.

[30] Foreign Application Priority Data

Aug. 20, 1976 [IE] Ireland .................. 1867/76

[51] Int. Cl.³ .......................................... H01H 21/00
[52] U.S. Cl. ................... 200/85 R; 200/86 R; 200/333; 340/666
[58] Field of Search ............... 340/568, 573, 576, 665, 340/666; 307/116, 119; 200/61.7, 85 R, 86 R, 86 A, 153 T, 329, 330, 331, 332, 333

[56] References Cited

U.S. PATENT DOCUMENTS

| | | | |
|---|---|---|---|
| 1,758,546 | 5/1930 | Wartmann . | |
| 2,260,715 | 10/1941 | Ketchem | 200/85 R |
| 2,436,898 | 3/1948 | Rickmeyer | 200/159 |
| 2,458,192 | 1/1949 | Niles | 340/568 |
| 2,463,980 | 3/1949 | Lee | 200/85 A |
| 2,713,645 | 7/1955 | Lerch | 307/119 |
| 2,818,477 | 12/1957 | Gollhofer | 200/83 R |
| 3,273,038 | 9/1966 | Miller | 307/119 |
| 3,591,739 | 7/1971 | Kenton | 200/52 |
| 3,656,141 | 4/1972 | Hill | 340/272 |
| 3,824,536 | 7/1974 | Cherico | 340/52 R |
| 3,845,261 | 10/1974 | Blinkilde | 200/85 A |
| 3,852,736 | 12/1974 | Cook | 340/279 |
| 3,961,201 | 6/1976 | Rosenthal | 307/116 |
| 4,164,637 | 8/1979 | Miyazi | 200/86 R |
| 4,263,586 | 4/1981 | Nicholas | 340/568 |

FOREIGN PATENT DOCUMENTS

| | | |
|---|---|---|
| 438600 | 12/1926 | Fed. Rep. of Germany . |
| 2440029 | 3/1976 | Fed. Rep. of Germany . |
| 491879 | 6/1919 | France . |
| 420071 | 11/1934 | United Kingdom . |
| 1082411 | 9/1967 | United Kingdom . |
| 1145514 | 3/1969 | United Kingdom . |
| 1233467 | 5/1971 | United Kingdom . |
| 1308751 | 3/1973 | United Kingdom . |

Primary Examiner—G. P. Tolin
Attorney, Agent, or Firm—Sughrue, Mion, Zinn, Macpeak and Seas

[57] ABSTRACT

A pressure operated electrical switch and an alarm system for use in hospitals and nursing homes is constructed such that a force is applied to a pressure plate therein. Once the load is reduced below a predetermined value the pressure plate will move under spring influence to close/open a microswitch or electrical contact means. The normal force applied to the pressure plate is the load on the leg of the hospital bed when occupied. If the bed occupant gets out of the bed the load on the pressure plate is reduced below a predetermined value, and the consequent movement of the pressure plate opens/closes the switch means to actuate the alarm.

7 Claims, 21 Drawing Figures

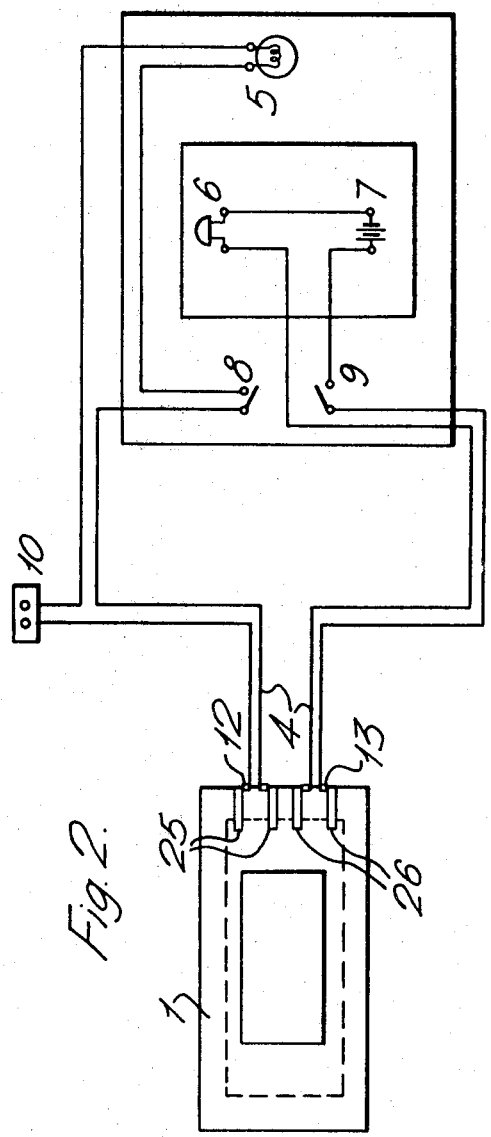
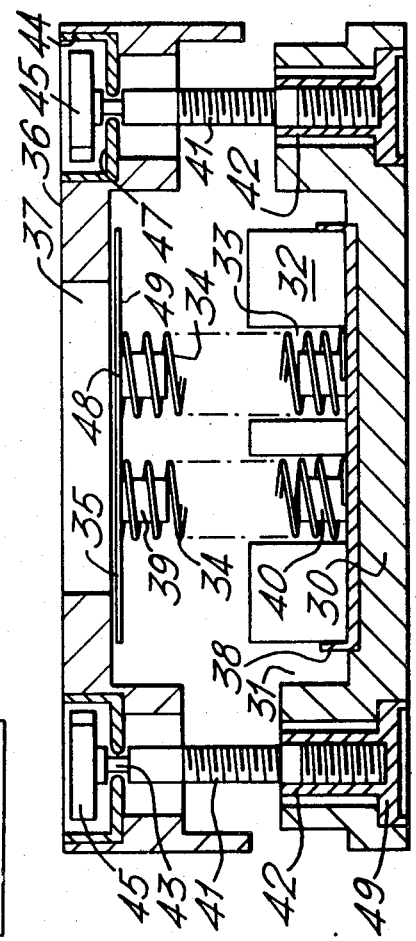

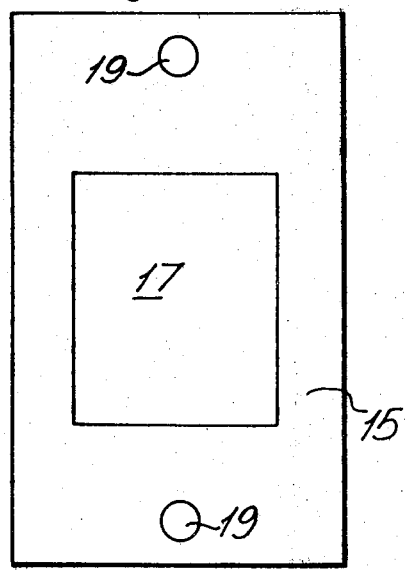
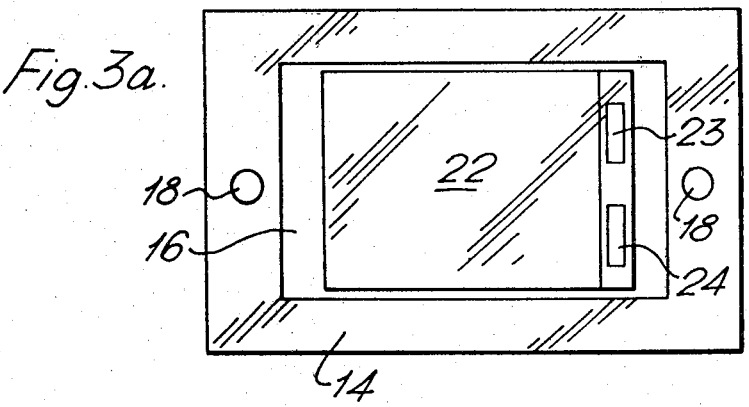
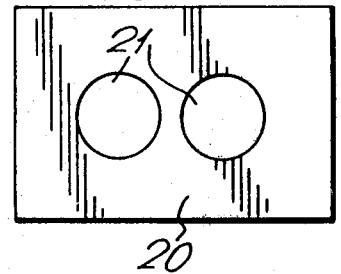
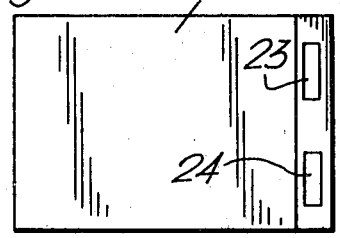

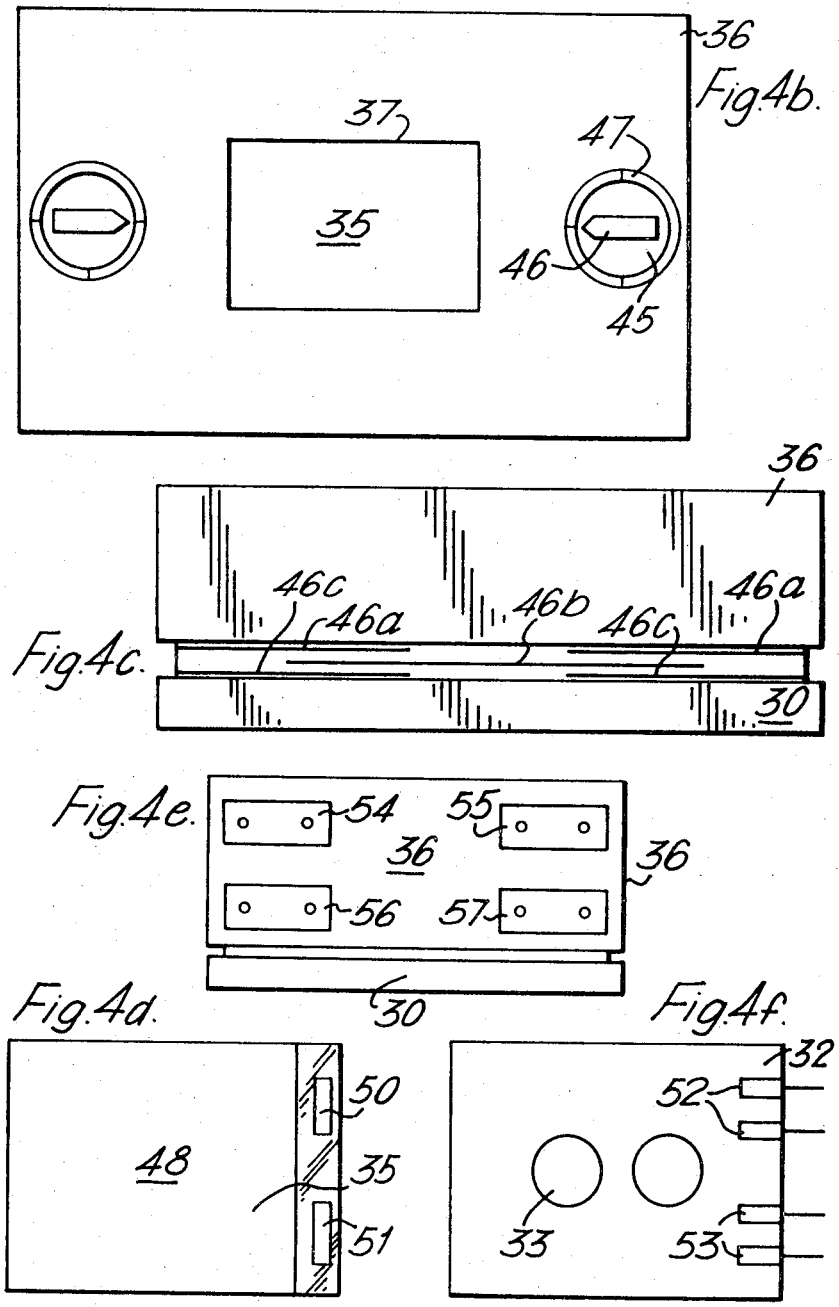

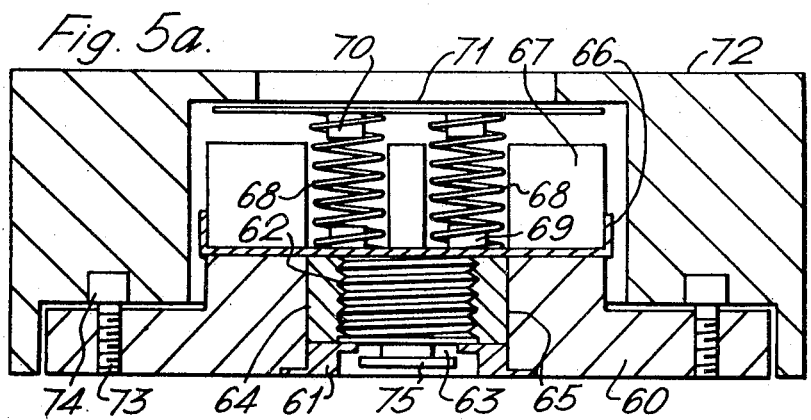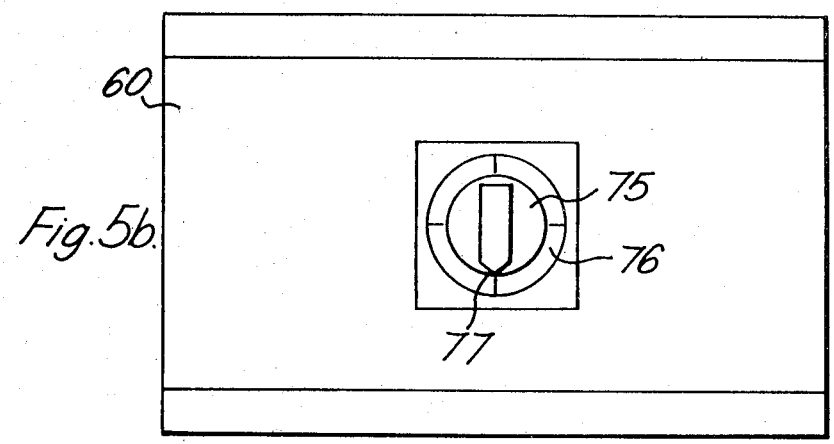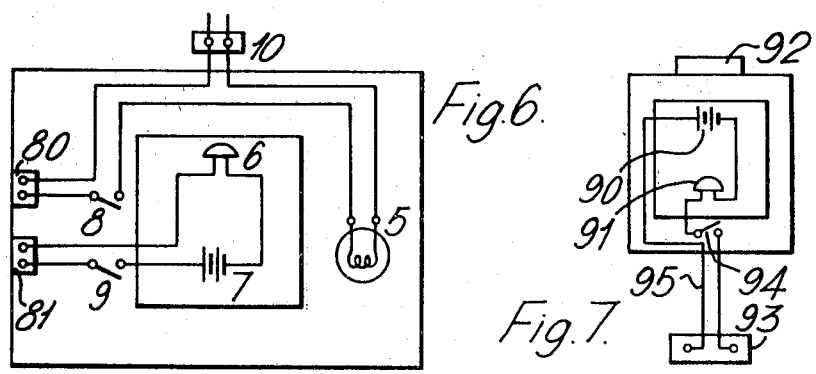

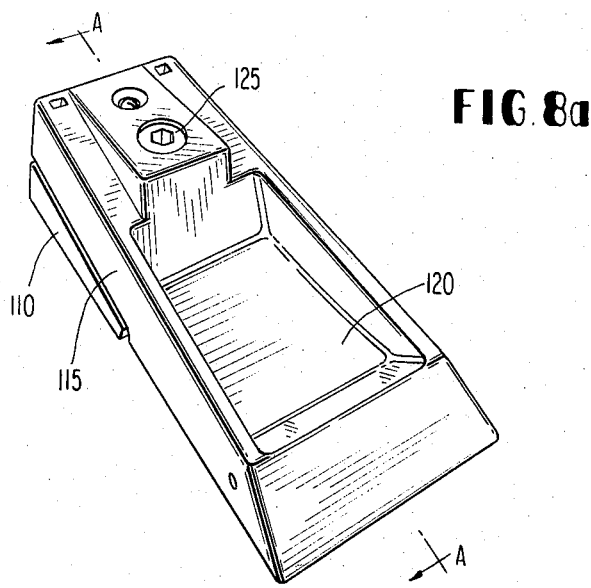
FIG. 8a
FIG. 8b
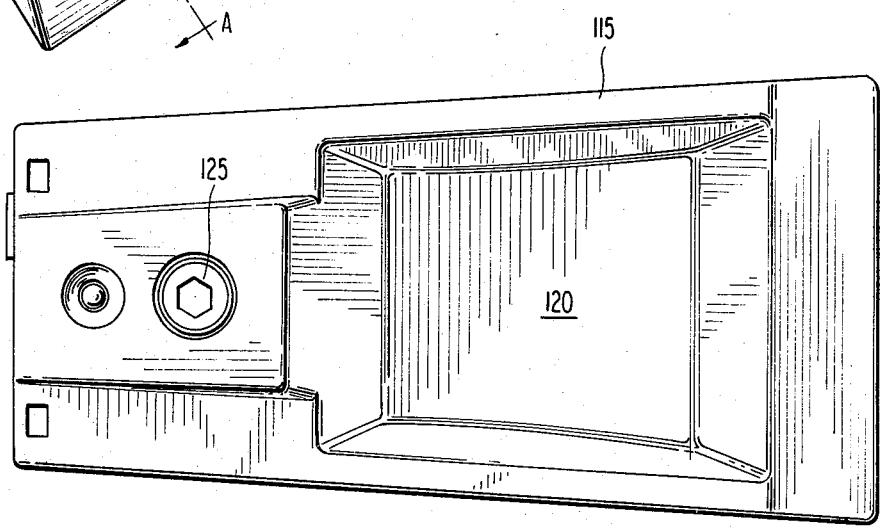
FIG. 8c
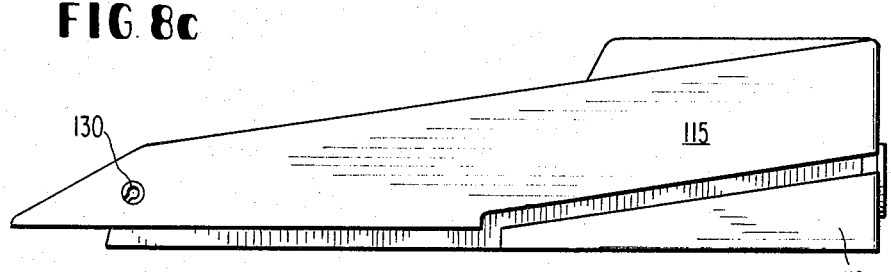
FIG. 8d
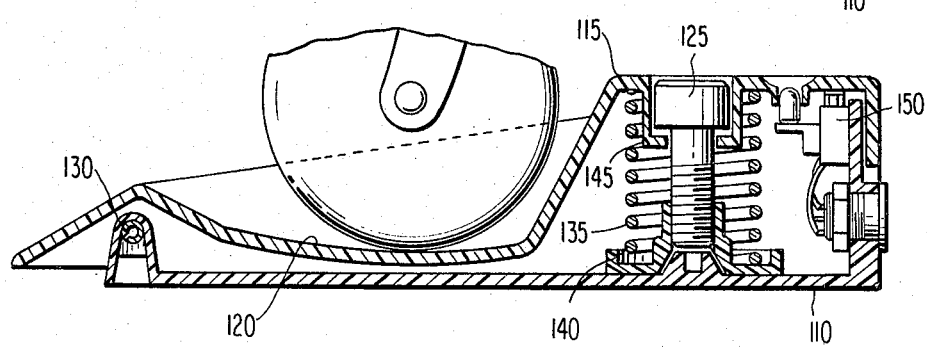

PRESSURE OPERATED ELECTRIC SWITCH AND ALARM SYSTEM USING SUCH SWITCH

CROSS REFERENCES TO RELATED APPLICATIONS

This application is a continuation-in-part of the co-pending application Ser. No. 907,461, for "Pressure Operated Electric Switch and Alarm System Using Such Switch", filed May 19, 1978, now U.S. Pat. No. 4,263,586, which was a continuation-in-part of application Ser. No. 826,957, for "Pressure Operated Electric Switch and Alarm System Using Such Switch", filed Aug. 22, 1977, now abandoned.

BACKGROUND OF THE INVENTION

The present invention relates to a pressure operated electric switch.

SUMMARY OF THE INVENTION

According to the invention there is provided a pressure-operated electric switch for use in conjunction with a bed and adapted for insertion under one leg of the bed to signal the absence of a patient therefrom, the switch comprising: a housing having a base portion and an overlying cover portion, at least a part of the cover portion being vertically movable relative to the base portion and being biased upwardly by compression spring means within the housing, the cover portion being recessed to provide a stable support for the leg of the bed on the vertically movable part, and switch means mounted in the housing for actuation upon vertical movement of said at least part of the cover portion with respect to the base portion, the switch means being actuated when an external downward load provided by the bed on said at least part of the cover portion exceeds a selected threshold value, and the compression spring means being supported at one end in the housing by a support member separate from the cover and base portions and vertically adjustable relative to the base portion in order to adjust the degree of compression of the compression spring means and thus the upward bias exerted by the compression spring means, such adjustment being provided by a screw-threaded element rotatable from outside the housing and operatively associated with the housing and support member in such manner that rotation of the element effects vertical movement of the support member relative to the base portion, whereby the threshold value at which said switch means is actuated is adjustable in respect of different weights of bed by rotation of the screw-threaded element.

In a preferred embodiment of the invention the cover portion and the said at least part thereof are constructed as a single element which is pivoted as a whole to the base portion at one end to allow vertical movement of the cover portion relative to the base portion, the stable support for the leg of the bed being provided by a shallow recessed part of the cover portion adjacent the pivoted end and the compression spring means being accommodated in an upstanding part of the cover portion remote from the pivoted end, the compression spring means biasing said upstanding part of the cover portion, and hence the shallow recessed part, upwardly from the base.

In use, the switch is acted on by a leg of the bed and the screw-threaded element is adjusted such that when the bed is occupied by the patient the pressure acting on the cover portion of the housing is sufficient to maintain the contacts of the switch means in, for example, the open position whereas when the bed becomes unoccupied the switch contacts move to the closed position to provide an alarm. The alarm may be audible and/or visible, e.g., it may comprise a bell and/or light.

It will be appreciated that the manner of adjustment of the degree of compression of the compression spring means according to the invention, being effected by providing a separate vertically movable support for the spring means within the housing which is adjustable in height from outside the housing by a screw-threaded element, permits the threshold value to be set, within limits, in a simple manner without changing the overall distance separating the cover portion from the base portion. This is particularly important in the preferred embodiment referred to above, since in that case the shallow recessed part of the cover portion is closely adjacent the underlying base portion. The overall dimensions of the switch, particularly in the vertical direction, are therefore substantially independent of the selected threshold value.

BRIEF DESCRIPTION OF THE DRAWINGS

Particular embodiments of the pressure operated electric switches and alarm systems incorporating switches are hereinafter described with reference to the accompanying drawings, in which:

FIG. 2 is a circuit diagram of the switch and alarm circuit of FIG. 1;

FIG. 3a is a plan view of the base of the switch of FIG. 1;

FIG. 3b is a plan view of the lid of the switch of FIG. 1;

FIG. 3c is a plan view of a housing for the main pressure springs of the switch of FIG. 1;

FIG. 3d is a plan view of the pressure plate of the switch of FIG. 1;

FIG. 3e is an end elevational view of the pressure plate of FIG. 3d;

FIG. 4a is a cross-sectional view of a second embodiment of the pressure-operated switch;

FIG. 4b is a plan view of the switch of FIG. 4a;

FIG. 4c is a side elevation of the switch of FIG. 4a;

FIG. 4d is a plan view of the pressure plate of the switch of FIG. 4a;

FIG. 4e is an end elevation of the switch of FIG. 4a;

FIG. 4f is a plan view of the spring mounting block of the switch of FIG. 4a;

FIG. 5a is a cross-sectional view of a third embodiment of the pressure-operated switch;

FIG. 5b is an underneath plan view of the switch of FIG. 5a;

FIG. 6 is a modification of the bedside alarm circuitry shown in FIG. 2;

FIG. 7 is a portable bell arrangement which may be used in conjunction with the pressure-operated switch;

FIG. 8a is a perspective view of a fourth and preferred embodiment of the pressure operated switch;

FIG. 8b is a top plan view of the switch shown in FIG. 8a;

FIG. 8c is a side view of the switch shown in FIG. 8a; and

FIG. 8d is a cross-sectional view along line 8a of the switch shown in FIG. 8a.

DESCRIPTION OF THE PREFERRED EMBODIMENTS

Figure 1:
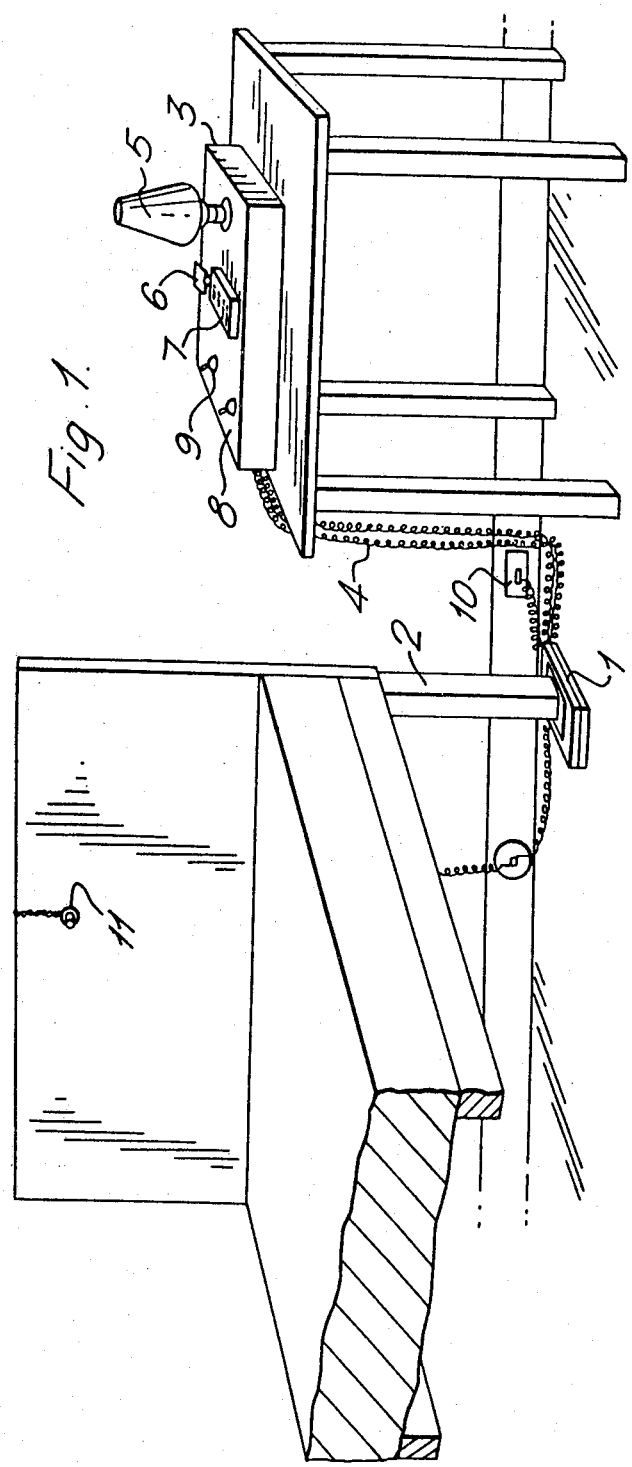
FIG. 1 is a schematic diagram of a switch and alarm circuit as installed in use so as to be operable by the leg of a bed.

As shown in FIG. 1, a pressure-operated electric switch 1 is positioned below the end of a bed leg 2 and is connected to an alarm circuit 3 by pairs of wires 4.

The alarm circuit 3 includes a light 5, a bell 6, a battery 7 for energizing the bell circuit, a switch 8 in the light circuit and a switch 9 in the bell circuit. The light circuit is energized from a main supply socket outlet 10. Normally, the switches 8, 9 are in the closed position but may be opened to interrupt the alarm. A push button switch 11 for use with the main house call bell is provided mounted on the bedhead. The circuit diagram of the alarm circuit is shown in FIG. 2.

The connection of the pairs of wires 4 to the switch 1 are preferably made by plug-and-socket connectors 12, 13, FIG. 2. Thus, a portable bell as shown in FIG. 7 may be plugged into the switch, or, when the alarm system is used in a house, the main house bell may be connected to the switch.

The switch 1 comprises a hollow box-like base 14, FIG. 3a, with a central cavity 16, and an overlying lid 15, FIG. 3b, which together with the base forms a hollow housing. The lid 15 has an aperture 17 for receiving the lower end of the bed leg 2. The lid 15 has depending side walls which surround the base 14 and is supported on the base by a pair of coiled springs (not shown) surrounding screw-threaded socket bolts or studs 18 upstanding from the base and extending through holes 19 in the lid. The upper ends of the springs abu the underside of the lid and the ends of the studs 18 extending through the lid holes 19 receive wing nuts bearing on the lid surface through washers.

The cavity 16 receives a spring housing 20 having apertures 21 for accommodating a pair of main coiled springs (not shown) for taking the load exerted by the bed leg. The housing 20 may be in the form of a block having a metal plate on its underside for closing the ends of the apertures 21. The upper ends of the main springs support a metal pressure plate 22, FIG. 3d, which is engaged on its upper surface by the bed leg 2 extending through aperture 17. The upper surface of the plate 22 carries a pair of bridging switch contacts 23, 24 which are insulatingly mounted on the plate. When the pressure exerted on the plate 22 by the leg 2 falls below a predetermined value, the plate is raised by the main springs so that the contacts 23, 24 bridge corresponding pairs of strip-type contacts 25, 26 mounted on the underside of the lid, FIG. 2. The contact pairs 25, 26 are connected, respectively, in the light and bell circuits by the plug-and-socket connectors 12, 13 and thus both the light and bell are energised to give the alarm.

To impart additional stability to the pressure plate 22 it may be provided on its underside with studs 27 which extend through the main coiled springs, FIG. 3e.

The pressure required on the plate 22 to separate the contacts 23, 24 from the contacts 25, 26 respectively, may be varied by adjusting the wing nuts on the socket bolts or studs 18 to vary the vertical spacing between the lid 15 and the base 14. Also, the pressure required to separate the contacts may be increased by inserting a packing plate between the base of the spring housing 20 and the floor of the base-cavity 16.

In one construction of the switch 1, the base 14, cover 15 and spring housing 20 are of wood, but any other suitable material may be used.

Referring now to the switch construction shown in FIGS. 4a to 4f, the switch comprises a base 30 with a central cavity 31 receiving a spring mounting block 32 having a pair of apertures 33 accommodating the lower ends of main springs 34. The upper ends of the springs 34 abut a pressure plate 35 and urge the plate towards the inner surface of a lid 36 having a central aperture 37 for receiving the leg of a bed. The block 32 is seated in a metal tray 38, and studs 39, 40 respectively are provided on the plate 35 and the tray 38 for stabilizing the springs 34. The lid 36 is supported on the base 30 by screw-threaded bolts 41 co-operating with screw-threaded socket 42 secured to the base, the upper ends of the bolts having reduced neck portions 43 co-operating with brackets 44 sunk into the top surface of the lid. The end of each bolt 41 has a knob 45 so that the bolts may be rotated to adjust the distance of the base from the lid and thus the pressure required to operate the switch. A pointer 46 on the knob registers on a circular scale 47 (FIG. 4b) provided on the lid. A further adjustment of the operating pressure may be obtained by inserting one or more packing plates beneath the tray 38. To permit rotating the knobs by e.g., a screwdriver, they may be provided with a slot. The screw-threaded sockets 42 are secured to the base by brackets 49 sunk into the base, the brackets 49 being of square cross-section for preventing rotation on the base.

To maintain even pressure adjustment between the two knobs 45, the base is provided externally with horizontal indicator lines 46a, b and c (FIG. 4c) for registering with the lower edge of the lid; also, the lines are indicative of the pressure setting. Thus line 46a indicates low pressure, line 46b medium pressure and line 46c high pressure.

The pressure plate 35, FIG. 4d, insulatingly carries on each of its upper and lower surfaces 48, 49, two bridging contacts 50, 51. FIG. 4d shows the two bridging contacts on the upper surface 48 and a similar pair of contacts, not shown, are provided on the lower surface 49. The contacts 50, 51 on the upper surface serve to bridge corresponding pairs of fixed contacts (not shown) provided on the under surface of the lid when the pressure plate 35 is biased by the springs 34 against the lid as shown in FIG. 4a. Two further pairs of contacts 52, 53, FIG. 4f, are provided on the upper surface of the block 32 and these are bridged by the bridging contacts on the underside of the pressure plate when sufficient force is applied to the plate to move it downwardly against the spring pressure. The two pairs of contacts carried by the lid are connected by wires to respective ones of the upper two plugs 54, 55 of four plugs 54–57, flush-mounted in one end of the lid 36, FIG. 4e, and the two pairs of contacts 52, 53 carried by the block 32 are similarly connected by wires to the lower plugs 56, 57.

The left-hand plugs 54, 56 serve for connection to the alarm bell circuit and the right-hand plugs 55, 57 serve for connection to the light circuit described previously with reference to FIG. 2. Thus, by inserting sockets into the lower or upper plugs, a choice may be made as to whether the alarm is to be given and the light energized either when the force acting on the pressure plate is increased or when it is decreased.

In the embodiment of the pressure-operated switch shown in FIGS. 5a and 5b, the switch base 60 has a central aperture 65, in which an annular bracket 61 is secured rotatably supporting a screw-threaded bolt 62, by co-operating with a reduced neck portion 63 of the bolt. A screw-threaded socket 64 in threaded engagement with the bolt 62, is slidably guided in the base aperture 65 and is attached to the underside of a metal tray 66, receiving a spring mounting block 67. The pair of springs 68 are stabilized by studs 69 on the tray 66 and studs 70 on a pressure plate 71. A lid 72 is attached to the base 60 by bolts 73, co-operating with sockets 74. Pairs of bridging contacts, not shown, are provided on the upper and lower surfaces of the pressure plate similar to those of FIGS. 4d, and pairs of contacts, not shown, are provided on the underside of the lid 72 and on the spring mounting block 67, similar to those described with reference to FIGS. 4a and 4f. Also, the end of the cover 72 has four sockets arranged similarly to those shown in FIG. 4e. In this embodiment the switch operating pressure is adjusted by rotation of the single bolt 62 by means of a knob 75, this action causing raising or lowering of the tray 66 relative to the lid 72. The knob 75 has a pointer 77 registering with a scale 76.

The bedside control panel circuitry shown in FIG. 6 is similar to that shown in FIG. 2 but includes sockets 80, 81 to enable connection to be made with the pressure-operated switch by means of flexible cables having plugs at each end, one end being inserted into the switch and the other end being plugged into the control panel.

FIG. 7 shows a portable bell 91 in a case having a carrying handle 92, the bell having a battery 90 controlled by a switch 94 and being provided with a flexible cable 95 having a plug 93 for connection to the pressure-operated switch.

FIGS. 8a through 8d illustrate a fourth embodiment of the pressure-operated switch. In the embodiment of FIGS. 8a through 8d, the upper cover portion 115 of the switch housing operates as both the overlying lid and the pressure plate for vertical as a whole movement relative to the base portion 110 of the switch housing. The overlying lid 115 is contoured with a vertically recessed portion 120 so as to position the bed leg on the overlying lid/pressure plate 115 in a stable manner. The overlying lid/pressure plate 115 is pivotally mounted on base 110 by means of hinge 130 provided therethrough. The other end of the overlying lid/pressure plate 115 is moveably supported over the base 110 by means of spring 135, FIG. 8d, mounted from support member 140 to receptacle 145. Support member 140 is separate from base 110, while receptacle 145 is integral with pressure plate 115. The spring 135 biases the overlying lid and pressure plate 115 upwardly to thereby allow vertical movement of the plate 115 with respect to the base 110 under the influence of the bed leg, or other pressure means, applied to the recessed portion 120 of lid 115. The amount of force that is required to toggle the microswitch 150 is adjustable by means of externally accessible screw 125 which is threadedly attached to the support member 140, clockwise rotation of the screw 125 serving to lift the support member 140 within the housing and thereby subject the spring 135 to an increasing degree of compression, the cover portion 15 being maintained at a fixed height above the base 110 by abutment of the lower end of the screw 125 on the base 110.

The microswitch 150 is mounted on the upper portion of the base 110 adjacent the lid/plate 115. As shown in FIG. 8d, the weight provided by an unoccupied bed leg is not sufficient to toggle the switch into an open position, and the switch 150 is therefore closed. Upon exceeding the predetermined threshold when the patient returns to the bed for example, the lid 115 will move downwardly to open the switch 150.

It will be readily appreciated that the alarm system of the present invention has particular application to hospitals and nursing homes. In such use it is desirable and technically feasible using known/conventional electrical and/or electronic components to integrate the alarm system of the present invention with existing nurse calling systems.

I claim:

1. A pressure-operated electric switch for use in conjunction with a bed and adapted for insertion under one leg of the bed to signal the absence of a patient therefrom, the switch comprising: a housing having a base portion and an overlying cover portion, at least a part of the cover portion being vertically movable relative to the base portion and being biased upwardly by compression spring means within the housing, the cover portion being recessed to provide a stable support for the leg of the bed on the vertically movable part, and switch means mounted in the housing for actuation upon vertical movement of said at least part of the cover portion with respect to the base portion, the switch means being actuated when an external downward load provided by the bed on said at least part of the cover portion exceeds a selected threshold value, and the compression spring means being supported at one end in the housing by a support member separate from the cover and base portions and vertically adjustable relative to the base portion in order to adjust the degree of compression of the compression spring means and thus the upward bias exerted by the compression spring means, such adjustment being provided by a screw-threaded element rotatable from outside the housing and operatively associated with the housing and support member in such manner that rotation of the element effects vertical movement of the support member relative to the base portion, whereby the threshold value at which said switch means is actuated is adjustable in respect of different weights of bed by rotation of the screw-threaded element.

2. A switch according to claim 1, wherein the cover portion comprises a lid fixed relative to the base portion and a vertically movable pressure plate mounted in the housing immediately below the lid and upwardly biased by the compression spring means, the lid having an aperture exposing a portion of the upper surface of the pressure plate and the edges of the aperture together with the upper surface of the pressure plate defining said recessed stable support for the leg of the bed.

3. A switch according to claim 2, wherein the switch means comprises a first contact means carried by the pressure plate and a second contact means supported in the housing at a position for engagement by the first contact means at a given vertical position of the pressure plate.

4. A switch according to claim 2, wherein the compression spring means is supported at its lower end by the said vertically adjustable support member and supported at its upper end by means fixed relative to the underside of the pressure plate, and wherein the screw-threaded element extends upwardly through the base portion for screw-threaded engagement with the support member.

5. A switch according to claim 1, wherein the cover portion and the said at least part thereof are constructed as a single element which is pivoted as a whole to the base portion at one end to allow vertical movement of the cover portion relative to the base portion, the stable support for the leg of the bed being provided by a shallow recessed part of the cover portion adjacent the pivoted end and the compression spring means being accommodated in an upstanding part of the cover portion remote from the pivoted end, the compression spring means biasing said upstanding part of the cover portion, and hence the shallow recessed part, upwardly from the base.

6. A switch according to claim 5, wherein the switch means comprises a microswitch carried by the base portion at a position engageable by the cover portion upon downward vertical movement of the latter when the external force on the shallow recessed part of the cover portion exceeds the adjustable threshold value.

7. A switch according to claim 5, wherein the compression spring means is supported at its lower end by said vertically adjustable support member and is supported at its upper end by means fixed relative to the underside of the upstanding part of the cover portion, and wherein the screw-threaded element extends downwardly through the upstanding part of the cover portion for screw-threaded engagement with the support member.

* * * * *